United States Patent
Lutter (10) Patent No.: US 7,338,467 B2
(45) Date of Patent: Mar. 4, 2008

(54) DEVICE FOR MINIMALLY INVASIVE INTRAVASCULAR AORTIC VALVE EXTRACTION

(75) Inventor: Georg Lutter, Kiel (DE)

(73) Assignee: Universitatsklinikum Freiburg, Freiburg (DE)

( * ) Notice: Subject to any disclaimer, the term of this patent is extended or adjusted under 35 U.S.C. 154(b) by 101 days.

(21) Appl. No.: 10/510,378

(22) PCT Filed: Apr. 17, 2003

(86) PCT No.: PCT/EP03/04087

§ 371 (c)(1), (2), (4) Date: Nov. 23, 2004

(87) PCT Pub. No.: WO03/089041

PCT Pub. Date: Oct. 30, 2003

(65) Prior Publication Data

US 2005/0171472 A1    Aug. 4, 2005

(30) Foreign Application Priority Data

Apr. 19, 2002  (DE) ............................... 102 17 559

(51) Int. Cl.
*A61M 29/00* (2006.01)
*A61M 31/00* (2006.01)
*A61M 37/00* (2006.01)

(52) U.S. Cl. ............................ 604/101.01; 604/96.01; 604/101.03; 604/103.11; 604/509

(58) Field of Classification Search ............. 604/96.01, 604/101.01, 101.03, 101.04, 101.05, 102.01, 604/102.02, 102.03, 103.07, 103.11, 500, 604/506–509, 103.02, 103.04, 103.06, 103.08
See application file for complete search history.

(56) References Cited

U.S. PATENT DOCUMENTS

| 4,445,892 A |   | 5/1984  | Hussein et al. |
|---|---|---|---|
| 4,771,777 A |   | 9/1988  | Horzewski et al. |
| 5,163,905 A | * | 11/1992 | Don Michael ......... 604/101.03 |
| 5,195,969 A | * | 3/1993  | Wang et al. ............. 604/96.01 |
| 5,370,685 A |   | 12/1994 | Stevens |

(Continued)

FOREIGN PATENT DOCUMENTS

| DE | 199 04 975 A1 | 9/2000 |
|---|---|---|
| WO | WO93/01768 | 2/1993 |

*Primary Examiner*—Kevin C. Sirmons
*Assistant Examiner*—Bhisma Mehta
(74) *Attorney, Agent, or Firm*—Cahn & Samuels, LLP (57) ABSTRACT

A perfusion catheter includes at least one perfusion channel and at least two dilation units disposed at a distance from each other at the distal catheter region in the longitudinal extension of the catheter. Both of the at least two dilation units are projected through by the perfusion catheter and form, in an inflated state, an at least practically fluid-tight occlusion with the aortic wall. At least the dilation unit disposed on the proximal side has at least one passage through which an auxiliary catheter can be introduced in a fluid-tight manner. The perfusion catheter may have a working channel with an outlet opening in the region between the two dilation units and through which at least one auxiliary catheter can be introduced for aortic valve ablation.

17 Claims, 6 Drawing Sheets

U.S. PATENT DOCUMENTS

| | | |
|---|---|---|
| 5,460,610 A | 10/1995 | Michael |
| 5,462,529 A * | 10/1995 | Simpson et al. ....... 604/101.04 |
| 5,545,135 A | 8/1996 | Iacob et al. |
| 5,674,198 A | 10/1997 | Leone |
| 5,738,652 A * | 4/1998 | Boyd et al. .............. 604/96.01 |
| 5,814,016 A * | 9/1998 | Valley et al. ............ 604/96.01 |
| 5,840,081 A | 11/1998 | Andersen et al. |
| 5,855,601 A | 1/1999 | Bessler et al. |
| 6,090,096 A * | 7/2000 | St. Goar et al. ............. 604/509 |
| 6,168,624 B1 | 1/2001 | Sudai |
| 6,210,365 B1 * | 4/2001 | Afzal .................... 604/101.03 |
| 6,299,597 B1 * | 10/2001 | Buscemi et al. ....... 604/101.03 |
| 6,673,040 B1 * | 1/2004 | Samson et al. ........ 604/101.01 |
| 7,189,250 B2 * | 3/2007 | DoBrava et al. ............. 606/194 |
| 2002/0013569 A1 | 1/2002 | Sterman et al. |
| 2002/0120234 A1 * | 8/2002 | Kong .................... 604/103.07 |

\* cited by examiner

DEVICE FOR MINIMALLY INVASIVE INTRAVASCULAR AORTIC VALVE EXTRACTION

This application is a 371 U.S. national stage application of international application PCT/EP03/04087 filed Apr. 17, 2003, which claims priority of German patent application 102 17 559.4 filed Apr. 19, 2002.

TECHNICAL FIELD

DEVICE FOR MINIMALLY INVASIVE INTRAVASCULAR AORTIC VALVE EXTRACTION The present invention relates to a device for minimally invasive intravascular aortic valve extraction (PAVA=percutaneous aortic valve ablation) inside the human aorta.

PRIOR ART

Defects in the cardiac valve characterized either by a valve insufficiency, i.e. the cardiac valves are no longer able to close completely or by stenosed valves, i.e. the valves do not open completely, frequently are a combination of both valve insufficiency as well as stenosis. In the case of cardiac valve insufficiency, the blood flows back through the leaking valve with every heart beat so that the part of the heart upstream in the flood flow is burdened with additional fluid volume. Generally such type valves are replaced with artificial valves. When valves have constricted respectively have stenosed, usually the edges of the valve folds have grown together or have hardened as a result of arteriosclerotic deposition. As a consequence, the valves can only open partially and allow only part of the blood flow to pass. The part of the heart upstream in the blood flow of the stenosed valve is forced to use greater pressure to pump the blood through. Thus, if the heart exceeds its capacities, the consequence is cardiac insufficiency.

Fundamentally, there are two types of cardiac valve surgery available. If a cardiac valve is to be replaced, the natural cardiac valve is removed and replaced with a bio-prothesis or a mechanical cardiac valve. For this type of surgery, it is essential that there is no blood in the operation area, i.e. the natural blood flow is detoured. However, this is also the case if a cardiac valve or parts of a cardiac valve are to be reconstructed.

However, if the natural valve needs only to be dilated, without completely replacing it, dilation can be carried out within the scope of minimally invasive surgery with the aid of a dilatable element which is introduced into the valve. Such type of minimally invasive surgery is usually conducted by a cardiologist using suited cardiac catheter instruments that are introduced into the to-be-treated section of the heart via the patient's natural blood vascular system.

For example, in this context, reference is made to the document U.S. Pat. No. 5,840,081 which describes a device for implanting an artificial cardiac valve. In this case, the catheter is provided at its distal end with a dilatable stent, which can be widened with the aid of an inflatable balloon pressing the damaged natural cardiac valve against the wall of the blood vessel and covering the interior of the blood vessel with an artificial cardiac valve membrane.

A similar device can be found in DE 199 04 975 A1, which describes a device for intravascular cardiac valve surgery suited for implantation of a flexible cardiac valve prothesis in the case of cardiac valve insufficiency.

However, if specifically the diseased cardiac valve is to be extracted, with present medical means, extraction is inevitably conducted in medically very complicated, intensive open-heart surgery, in which the patient is attached to a heart-lung machine to maintain extracorporeal circulation with the exclusion of the to-be-treated heart. Despite the fact that the surgical procedure has been successfully conducted for quite some time, extraction, respectively ablation, for example of the aortic valve is very complicated to conduct.

This circumstance indicates that alternative considerations to carry out cardiac valve extraction in a minimally invasive manner will encounter even greater difficulties than conventional surgical procedures described in the preceding already do. One problem is that the valve has to be removed under great pressure in the blood stream.

WO 93/01768 describes a catheter system for minimally invasive intravascular aortic valve extraction, with which the extremely difficult manner of minimally invasive cardiac valve extraction described in the preceding is carried out. The catheter introduced through the natural human blood vascular system described in this printed publication is provided with a working channel at the distal end of which a working capsule is disposed inside of which a unfoldable, sieve-like designed umbrella element is provided. This element is positioned downstream of the aortic valve, and the aortic valve is severed locally with the aid of a rotating cutting tool which is then pushed through the working channel to the aortic valve. Aortic valve fragments that may have entered the blood stream as a result of the severing procedure should be caught by the umbrella-like element and can be sucked off to the outside through the working channel. Although the idea of minimally invasive aortic valve extraction using the catheter arrangement described in the preceding printed publication looks very promising, the prior art device has considerable drawbacks. First, a single umbrella cannot prevent aorta fragments from entering the aorta arch. As a consequence, there is a great risk of embolism. Secondly, the minimally invasive surgery is being performed in the pulsing, beating heart through which blood is circulating so that it is difficult for the surgeon to position the catheter arrangement precisely in the millimeter range in relation to the diseased cardiac valve. Moreover, the operation is carried out using visualization technology, for example radioscopy, on the basis of which the surgeon has to carry out extremely precise positioning procedures with the catheter instrument. An operation which demands extreme concentration of the surgeon. Furthermore, as observation technology is only indirect, it cannot be ruled out that surrounding healthy tissue of the aorta vessel wall is damaged during the actual aortic valve ablation by the rotating cutting arrangement.

U.S. Pat. No. 5,855,601 describes a similar catheter arrangement for minimally invasive cardiac valve replacement. For local cardiac valve ablation, a hollow catheter is provided having a dilatable reception unit at its distal end. This dilatable reception unit is able to snuggle, preferably funnel-shaped and fluid-tight, to the aortic wall in direct proximity on the proximal side in relation to the cardiac valve. Furthermore, a cutting catheter is provided which is pushed on the distal side through the diseased cardiac valve through the hollow catheter. Provided at the distal end of the cutting catheter is an inflatable protection balloon, at a distance on the proximal side of which a foldable cutting instrument is disposed. The cardiac valve is ablated by rotation of and movement on the proximal side of the cutting catheter with the aid of the rotating cutting instrument. The balloon provided at the distal end of the cutting catheter acts for the surgeon as a perceivable mechanical stop against the remaining not-to-be-removed circumferential edge of the cardiac valve so that the surgeon is informed in this manner that the cutting instrument has completely severed the cardiac valve along its movement in the proximal direction. Moreover, the inflatable balloon provided at the distal end of the cutting catheter acts as protection for the surrounding tissue area against the sharp-edged cutting instrument. Therefore, in an inflated state, the protection balloon has a diameter that is slightly larger than the diameter of the open, rotating cutting instrument.

The afore described catheter arrangement for cardiac valve ablation also proved unsatisfactory for use in heart catheter surgery as during the actual ablation procedure, the surgeon cannot ablate the cardiac valve areas individually. But rather, due to the centered guidance of the catheter and the distal end disposal of the protection balloon, the ablation instrument is aligned practically in the center in relation to the cardiac valve so that with corresponding rotation of the cutting instrument, only circular ablation is possible inside the cardiac valve. Particularly, in cases in which the diseased, to-be-ablated cardiac valve area is not circular in shape, it is impossible to conduct total cardiac valve extractions with the prior art catheter arrangement without risking damaging healthy aortic wall tissue. Furthermore, as the surgeon, like in the afore described case, only has conventional visualization technology at disposal to monitor the operation. The related problems have already been mentioned in the preceding described case. Finally, it needs to be pointed out that despite the provision of a protection balloon at the distal end of the ablation catheter, it cannot be guaranteed that severed cardiac valve fragments do not manage to enter the aortic arch. Consequently, with this surgical technique too, there still remains a risk of embolism.

DESCRIPTION OF THE INVENTION

The object of the present invention, therefore, is to improve and provide a device for minimally invasive, intravascular aortic valve extraction which completely rules out any risk of embolism from tissue particles and/or calcium particles that might enter the blood stream during aortic valve extraction. Furthermore, the surgeon should be able to ablate diseased cardiac valve areas individually locally and selectively, preferably under direct optical observation of the diseased cardiac valve areas. In particular, handling of the device should be facilitated for the surgeon in such a manner that signs of fatigue which may set in due to the great concentration required to conduct the operation can be completely ruled out.

A further object of the present invention is to provide a respective method for minimally invasive, intravascular aortic valve extraction.

An element of the present invention is that a device for minimally invasive, intravascular aortic valve extraction inside the aorta is designed in such a manner that a perfusion catheter is provided comprising at least one perfusion channel and at least two dilation units disposed at a distance from each other in the vicinity of the distal end of the catheter along the longitudinal extension of the catheter, both dilation units being penetrated by the perfusion channel and forming, in an inflated state, an at least almost fluid-tight occlusion with the vessel wall, preferably with the aortic wall. Of these two dilation units, at least the one disposed on the proximal side is provided with a passage through which at least one auxiliary catheter can be introduced in a fluid-tight manner for aortic valve ablation and/or the perfusion catheter is provided in the region between the two dilation units with at least one working channel with an outlet through which at least one auxiliary catheter can be introduced for aortic valve ablation.

The invented device is based on the idea of being able to conduct minimally invasive surgery on the beating heart without major impairment of the heart activity in order to carry out cardiac valve extraction while completely ruling out any risk of embolism, which hitherto was connected with such an operation.

For this purpose a perfusion catheter is provided that essentially encloses a hollow channel through which blood flow can be maintained. Prior art perfusion catheters, such as for example the ones described in U.S. Pat. No. 5,545,135, are fundamentally for dilation of stenosed regions of vessels and are provided on the exterior wall of the catheter with a dilation unit, which is inflated after corresponding placement of the catheter at a stenosed vessel site, thereby dilating the stenosed vessel wall. Such type perfusion catheters may be designed as rigid or flexible catheters, however, they always enclose an interior hollow channel required for maintaining blood flow.

In contrast to the prior art perfusion catheters, the device designed according to the present invention is provided with two dilation units disposed at a distance from each other in the longitudinal extension in the vicinity of the distal end of the catheter, namely one dilation unit on the distal and another one at a distance from it on the proximal side. Both dilation units are preferably designed as inflatable balloon elements and have in a particularly preferred embodiment a toroidal ring shape, with the perfusion catheter penetrating both dilation units through their central, ring-shaped protrusion in a fluid-tight manner. The size, distance and arrangement of the dilation units along the catheter axis of the perfusion catheter are selected in such a manner that the catheter arrangement can be pushed through the human vascular system into the region of the human heart preferably via the abdominal artery.

In particular, the object is to position the catheter arrangement designed according to the present invention inside the ascending aorta in such a manner that the dilation unit disposed on the distal side of the perfusion catheter can be positioned under the aortic valve, i.e. inside the left ventricle, and the dilation unit disposed on the proximal side lies above the aortic valve, i.e. inside the ascending aorta. The two dilation units disposed at a distance from each other in the longitudinal direction of the catheter usually are spaced approximately 2 cm apart in an inflated state and surround the aortic valve itself upstream and downstream with relation to the aortic region through which blood circulates and in which the aortic valve is located. The shape and size of the two dilation units are selected in such a manner that they form in an inflated state a fluid-tight occlusion with the respective vessel wall. In detail, this means that the dilation unit disposed on the proximal side forms a fluid-tight occlusion with the aortic wall inside the ascending aorta, whereas the dilation unit disposed on the distal side, which is located in the region of the left ventricle, in particular in the left ventricular outflow tract (LVOT) of the left ventricle, forms a fluid-tight occlusion with the vessel walls present in this area.

In the inflated state, i.e. the expanded state, the diameters of the dilation units preferably range between 0.3 and 2.5 cm.

The invented arrangement of the two dilation units along the perfusion catheter permits enclosing a volume which contains the aortic valve and which is surrounded by the dilation units and the vessel wall bordering the dilation units.

When the dilation units are inflated, this volume is decoupled from the natural blood stream. Despite the achieved interruption of the natural blood flow inside the aorta in the cardiac valve region, practically unrestricted heart activity can be maintained as a sufficient amount of blood volume is able to enter the ascending aorta from the left ventricle through the hollow channel of the perfusion catheter.

In order to reduce the increased flow resistance along the hollow channel of the perfusion catheter caused by the perfusion catheter, an advantageous preferred embodiment provides a pump device which preferably is integrated inside the perfusion catheter and conveys blood from the left ventricle into the ascending aorta. For this purpose, the perfusion catheter is provided at its distal-side catheter end, which projects on the distal side beyond the dilation unit disposed on the distal side, with a corresponding inlet opening through which blood enters, respectively is sucked into, the hollow channel of the perfusion catheter. In the same manner, a corresponding outlet opening is provided on the proximal side in relation to the dilation unit disposed on the proximal side, through which the blood flow exits with corresponding positioning of the perfusion catheter in the ascending aorta.

In this manner, the natural blood flow in the heart is maintained largely without restriction despite the intracorporeally introduced catheter arrangement.

In order now to be able to selectively operate on the cardiac valve enclosed by the two dilation units in an inflated state, at least one auxiliary catheter has to be introduced into the region of the working volume enclosed by the two dilation units. Fundamentally, there are two possible ways to do this, which can be realized alternatively or in combination:

On the one hand, the dilation unit disposed on the proximal side is provided with at least one passage through which at least one auxiliary catheter can be passed in a fluid-tight manner after corresponding positioning of the perfusion catheter arrangement in relation to the cardiac valve. On the other hand, at least one additional working channel can be provided inside the hollow channel. The additional working channel is provided in the region between the two dilation units with an outlet opening inside the perfusion catheter wall through which a corresponding auxiliary catheter can be introduced into the region of the to-be treated cardiac valve.

In order to conduct successful surgery on the cardiac valve, for example for selective local or total extraction, respectively ablation, the dilation unit disposed on the proximal side is provided with further passages through which suited catheter instruments can be introduced into the working volume. Thus, for example, introduction of two additional so-called coronary perfusion catheters is required in order to maintain blood flow in the left and right coronary arteries, which are separated from the natural blood circulation during positioning of the perfusion catheter with the two dilation units described in the preceding. For suited positioning and introduction of the additional, required coronary perfusion catheters, the dilation unit disposed on the proximal side is provided with two corresponding passages which occlude in a fluid-tight manner with the coronary perfusion catheters.

The coronary perfusion catheters themselves are provided at their distal ends respectively with a dilatable balloon, a so-called cuff by means of which the coronary perfusion catheters themselves form a fluid-tight occlusion with the inlet opening of the left, respectively the right coronary artery. Blood circulation in the coronary arteries occurs after corresponding positioning of the coronary perfusion catheters via blood from the abdominal region by means of suited abdominal catheters and/or if need be by means of an interconnected external or internal pump.

In an especially advantageous manner, the dilation unit disposed on the proximal side is provided with passages via which an optical observation catheter can be introduced into the working volume. Furthermore, passages are provided for connection to a suction line and a corresponding rinsing line in order to pump the working volume empty of blood. In this manner, the surgeon obtains by means of the optical observation catheter a direct free view of the to-be-treated cardiac valve, which he can ablate with a suited catheter ablation instrument under direct observation.

With the aid of two dilation units disposed along the perfusion catheter, the invented device permits for the first time creating a blood-empty working volume around the to-be-treated aortic valve. Inside this blood-empty volume, the surgeon can treat the aortic valve in a suited manner under direct observation using suited catheter instruments. The entire operation occurs on the beating heart thereby obviating as far as possible use of a heart-lung machine.

Moreover, fluid-tight occlusion with the aid of the two inflatable dilation units ensures that any separated valve fragments can be conveyed safely extracorporeally out of the working region via a suited suction line. Furthermore, the working volume that is separated fluid-tight from the other blood volume can be continuously cleaned with a suited rinsing liquid so that it can be ruled out that any ablated particles remain inside the working volume, which should completely prevent any risk of embolism. In addition to this, the coronary surgery to be conducted can be performed without any time pressure as any hemodynamic impairment of the heart can be ruled out because it has been at the same time ensured that blood circulates in the coronary arteries and hemodynamics are maintained with the aid of the perfusion catheter.

When the operation has ended, the catheter instruments required for the aortic valve ablation are removed extracorporeally out of the working volume through the respective passages and the dilation units are deflated. Then the entire perfusion catheter can be drawn out of the human vascular system without any risk.

In the event of a total cardiac valve extraction, however, it is necessary to at least implant a cardiac valve prosthesis, which takes over the function of the cardiac valve interim, before the perfusion catheter positioned inside the aorta arch is removed extracorporeally. For this purpose, in a preferred embodiment a sluice also comprising a dilation unit is provided on the proximal side in relation to the dilation unit disposed on the proximal side along the perfusion catheter. The sluice can either be introduced after positioning of the perfusion catheter or can be introduced intracorporeally along with the perfusion catheter. The dilation unit representing the additional sluice remains in the region of the ascending aorta even after removal of the perfusion catheter and is able to take over the function of the extracted cardiac valve at least interim. For this purpose, the rhythm with which the additional dilation unit is inflated and deflated is EKG triggered in such a manner that the blood circulation is ensured corresponding to the natural heart rhythm.

The sluice operating and installed in this manner takes over the function of the cardiac valve missing as a result of extraction of the natural cardiac valve until a new cardiac valve, for example in the form of a cardiac valve stent is inserted.

BRIEF DESCRIPTION OF THE DRAWING

The present invention is made more apparent in the following without the intention of limiting the overall inventive idea using preferred embodiments with reference to the drawings depicting in.

WAYS TO CARRY OUT THE INVENTION, COMMERCIAL APPLICABILITY

Figure 1:
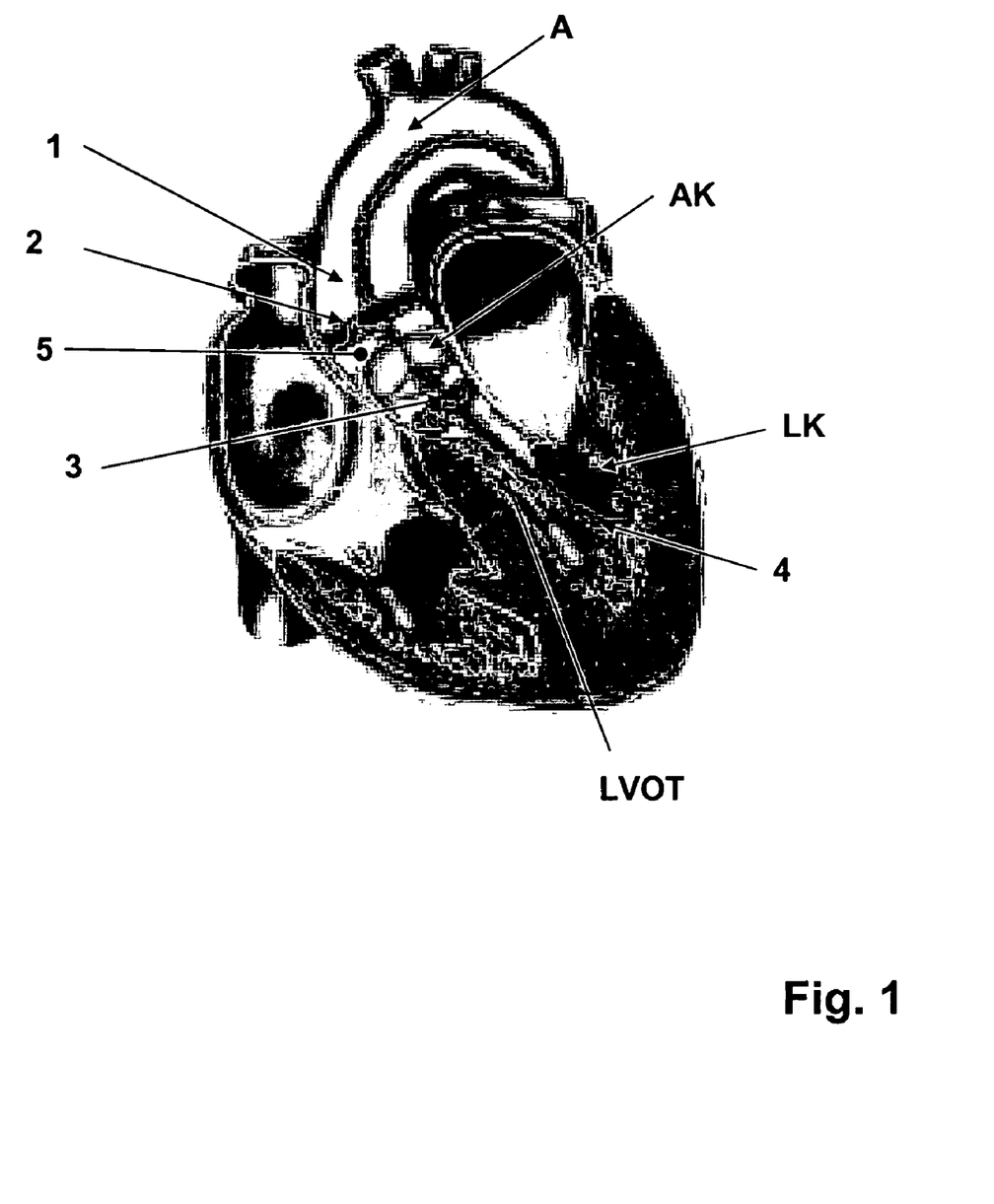
FIG. 1 a cross-sectional representation of a human heart with an inserted perfusion catheter arrangement, FIG. 2 a schematic representation of a perfusion catheter designed according to the present invention, FIG. 3 a top view (transversal section) of the dilation unit disposed on the proximal side, FIG. 4 a schematic cross-sectional representation (coronary section) of the perfusion catheter introduced intracorporeally in the region of the to-be-extracted cardiac valve, FIG. 5 a schematic representation of all the essential components for successful conduction of a cardiac valve extraction, and FIG. 6 an alternative embodiment of a dilation unit.

FIG. 1 depicts a cross section of a human heart showing the course of the aorta A (ascending aorta), the aortic valve AK located inside the aorta A and the left ventricular outflow region LVOT of the left ventricle LK. In detail, the aortic valve AK is to be extracted from aorta A in a manner that is gentle to the patient. For this purpose, the perfusion catheter 1 designed according to the present invention is provided with two dilation units 2,3, which are designed as inflatable balloon elements and which are positioned by means of the perfusion catheter 1 in relation to the aortic valve AK in such a manner that the dilation units 2,3 enclose the aortic valve AK on both sides in longitudinal direction to the aorta A. The dilation units 2,3 are dimensioned in such a manner that in a dilated state they form with the corresponding vessel walls of the aorta, respectively of the LVOT, a fluid-tight occlusion, creating in this manner, a fluid-tight working volume 5 inside which the cardiac valve AK is located.

Furthermore, in order to extract the cardiac valve AK, the working volume 5 must be emptied of blood in such a manner that the cardiac valve AK can be monitored and selectively ablated by the surgeon under direct optical observation as will be described in detail in the following. Any valve fragments present inside the working volume 5 cannot enter the adjacent blood stream due to the fluid-tight separation of volume 5 from the other regions of the vessel volume. But rather, such type fragments must be selectively conveyed extracorporeally via respective drainages, this too will be explained in more detail in the following. In order to be able to maintain the natural blood flow between the left ventricle LK and the aorta A even during the operation, the perfusion catheter 1 acts as a passage for blood flowing from the left ventricle LK into the aorta A.

Only for reasons of comprehensiveness, it is pointed out that the cross section of FIG. 1 shows a guiding catheter 4 extending into the left ventricle LK. This guiding catheter 4 acts as a navigation aid for the perfusion catheter 1 and is brought from the abdominal region of the to-be-treated patient into the position depicted in FIG. 1 before the perfusion catheter 1 is introduced through the human vascular system into the heart.

Figure 2:
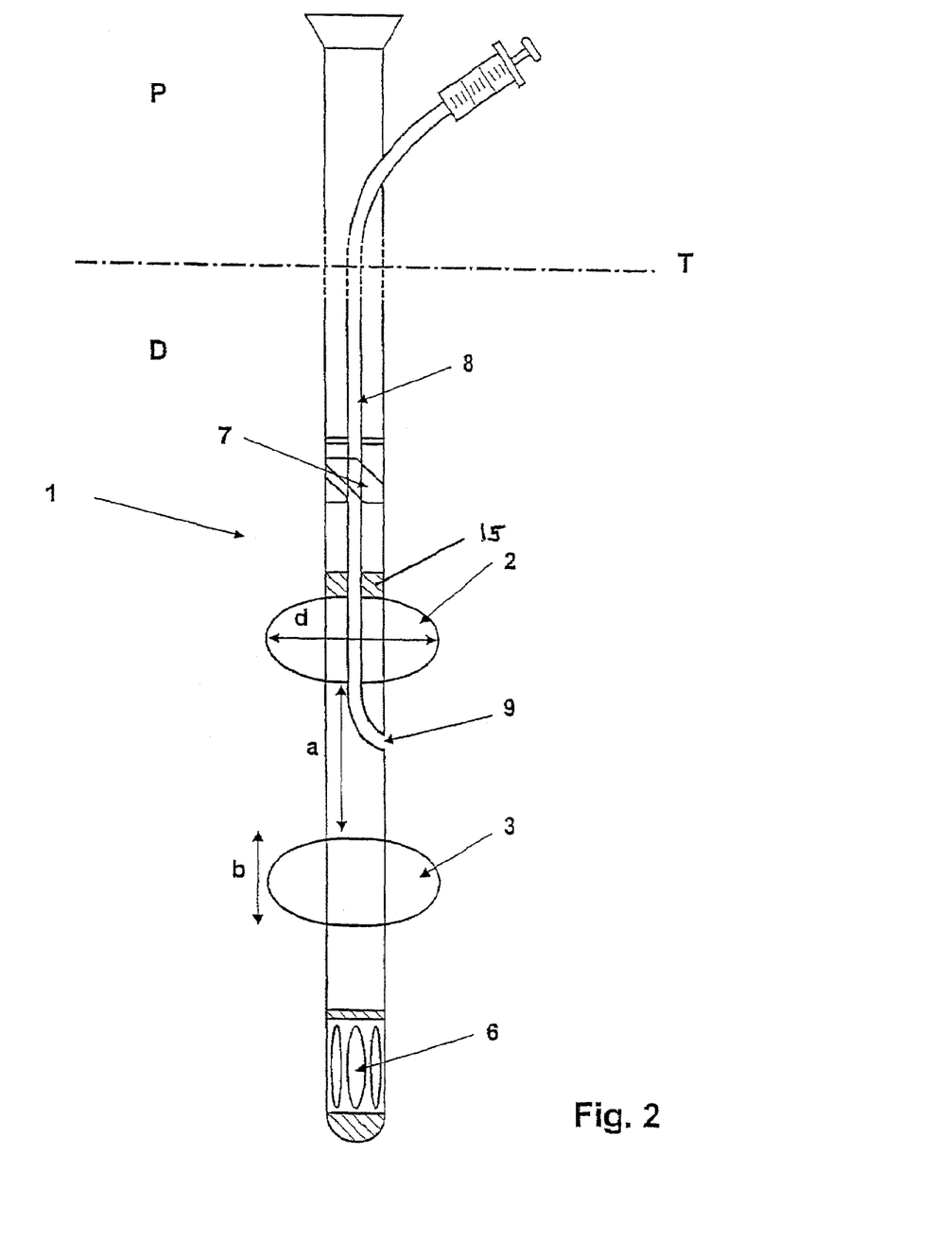

FIG. 2 shows a schematic representation of a concrete preferred embodiment of a perfusion catheter 1. For basic understanding of the figure, it is to be noted that the separation line T separating the distal catheter region D projecting into the heart region from the proximal catheter region P, which is connected with corresponding extracorporeal operating and introduction elements, which will not be given closer consideration, is entered solely for better graphic illustration.

The distal perfusion catheter region D is provided with two dilation units 2,3 which are disposed at a distance from each other in the longitudinal direction of the catheter. Usually the distance a is at least 1 cm, for example, approximately 2 cm. Both dilation units 2,3, which are designed as dilatable balloon elements, are penetrated in the center by perfusion catheter 1 and have in a dilated state usually a balloon diameter d of between 1.5 and 2.5 cm. In an expanded state, balloon thickness b is 0.5 to 1 cm usually. The dilation unit 3 disposed on the distal side is preferably located preferably 1 cm from the distal end of the perfusion catheter 1. Blood enters the inner hollow chamber enclosed by the perfusion catheter 1 through corresponding blood inlet openings 6 provided at the distal end of the perfusion catheter 1 and leaves the perfusion catheter again via the blood outlet openings 7, which are provided on the proximal side in relation to the dilation unit 2 disposed on the proximal side. At least the dilation unit disposed on the proximal side is disposed in a rotary moveable manner about the perfusion catheter.

Preferably the perfusion catheter 1 is provided with a pump device 15 in the region between the inlet and outlet openings 6,7 in order to maintain a blood flow which corresponds approximately to the natural pumping performance of a human heart. Alternative suction devices, which reinforce the blood flow directed through the perfusion catheter, for example by means of a suction pump connected extracorporeally to the hollow catheter of the perfusion catheter, may also be provided.

As described in detail in the following with reference to FIGS. 3 and 4, the dilation unit 2 disposed on the proximal side is provided with corresponding passages (not shown in FIG. 2), through which auxiliary catheter instruments can be introduced on the proximal side through the dilation unit 2 into the intermediate space between the two dilation units 2 and 3. In a preferred embodiment, the perfusion catheter 1 is provided with at least one working channel 8 running inside the perfusion catheter 1. Working channel is provided with an outlet opening 9, which is positioned between the two dilation elements 2,3. In this manner, the corresponding auxiliary catheter instruments can be introduced in the center of perfusion catheter 1 through the working channel 8 in order to be able to carry out surgical procedures on a cardiac valve, not depicted in FIG. 2, inside the working volume 5 (shown in FIG. 4) bordered by the two dilation units 2 and 3.

Figure 3:
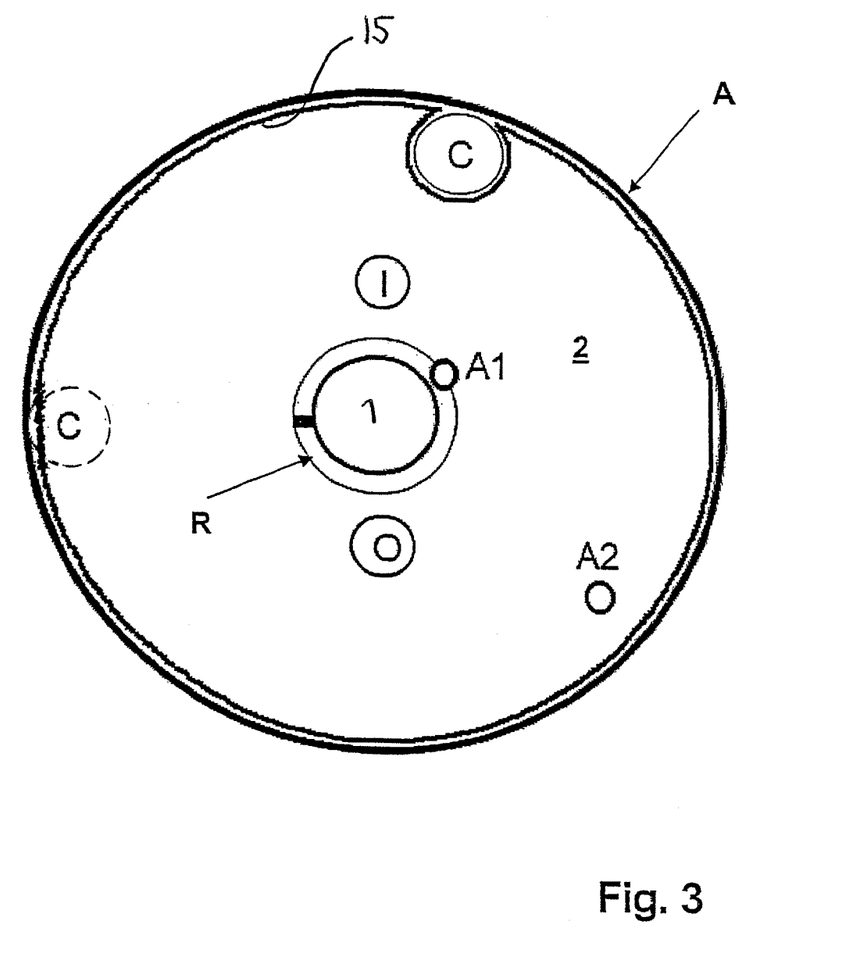

FIG. 3 shows a view in the distal direction of the dilation unit 2 disposed on the proximal side. In this view, the dilation unit 2 is inside the aorta A in an inflated state. The shape and size of the dilation unit 2 are selected in such a manner that in an inflated state the dilation unit 2 forms a fluid-tight occlusion with the wall of aorta A. Down the center through dilation unit 2 (as well as through dilation unit 3) projects the perfusion catheter 1 whose hollow channel serves to maintain the blood flow. In addition, dilation unit 2 is provided with a multiplicity of passages which act as fluid-tight passage openings for auxiliary and working catheters. Thus, the circumferential edge of the dilation unit 2 surrounds in a fluid-tight manner two coronary perfusion catheters C introduced in the longitudinal direction of the aortic wall. When the dilation unit is in an inflated state, part of the passage for coronary perfusion catheters is bound sickle-like by a circumferential edge of the dilation unit and a remaining part of the passage is bound by the aortic wall. The coronary perfusion catheters C ensure blood supply to the left and to the right coronary arteries during cardiac valve extraction. For this purpose, the coronary perfusion catheters C are provided at their distal end region with corresponding dilatable cuffs C' (FIG. 5) with which the coronary perfusion catheters can be placed and fixed inside the coronary arteries. The coronary arteries can be supplied, even during cardiac valve extraction, locally with blood from the abdominal region via abdominal catheters connected to the aforementioned coronary perfusion catheters C, if need be, using an interconnected external pump, in order to impede natural heart activity as little as possible.

In order to remove the blood from the working volume 5 bordered by the two dilation units 2,3, two additional passages I and O are provided inside the dilation unit 2, through which a suction catheter, respectively a rinsing catheter, can be introduced. After corresponding removal of the blood, an optical viewing catheter can be introduced into the working volume through the already present, respectively additional, passages in such a manner that the surgeon is able to observe the cardiac valve directly in situ. Furthermore, two further passages A1 and A2 are provided through which corresponding working, respectively ablating catheters can be introduced with which the surgeon can perform ablation of stenosed areas of the cardiac valve.

Through a passage A1, which can be moved in a fluid-tight manner along the periphery of the perfusion catheter 1 on an orbit around the perfusion catheter 1, provided directly on the circumferential edge of the perfusion catheter 1, the surgeon is able to place an ablation instrument for ablation of areas in the center of the cardiac valve. The passage A1 is disposed in a rotatable manner about the perfusion catheter 1, respectively with the aid of a rotatable ring seal R placed about the perfusion catheter 1.

For cardiac valve ablation on the outer valve regions near the walls of the aorta A, the passage A2 is provided through which a corresponding ablation catheter can also be introduced and is disposed in the dilation unit 2 near the aortic wall A.

In an especially preferred embodiment, the dilation unit 2 is borne fluid-tight and rotatable about the perfusion catheter 1 in such a manner that the surgeon is able to position the working catheters projecting into the working volume to a great extent freely in relation to the cardiac valve.

Figure 4:
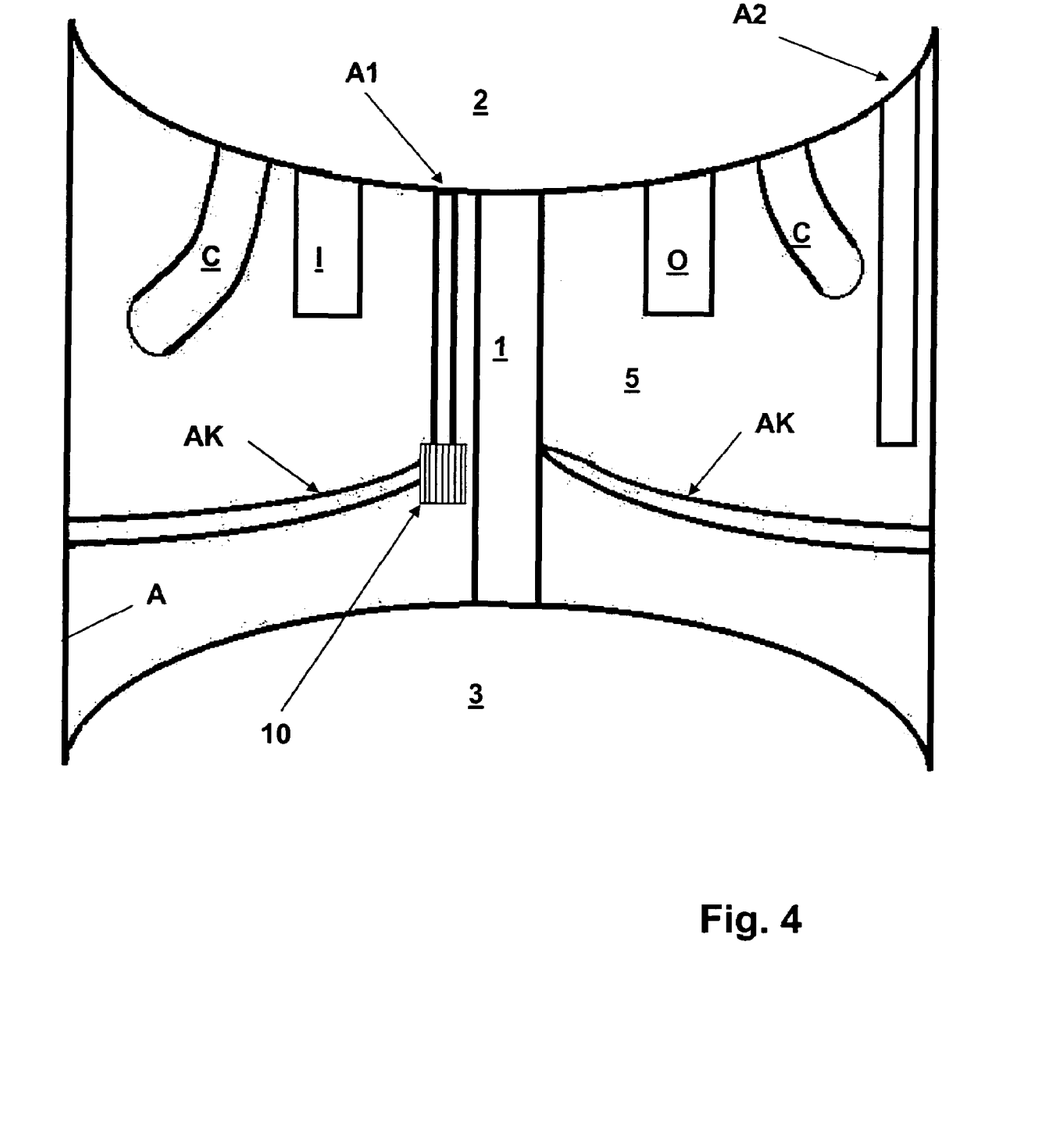

FIG. 4 shows a coronary section of the perfusion catheter 1 in the region of the working volume 5 enclosed by the dilation units 2,3 and the aortic wall A. The hollow channel of the perfusion catheter 1 projects through both the dilation unit 2 disposed on the proximal side and the dilation unit 3 disposed on the distal side. The aortic valve AK is located inside the working volume 5 and is separated in a fluid-tight manner from the remaining vascular system. Shown projecting through the dilation unit 2 are a number of auxiliary catheters, respectively supply lines and drainages, reaching through the dilation unit 2 into the working volume 5. Thus, two coronary perfusion catheters C pass through the corresponding passages through the dilation element 2 laterally into the coronary arteries to supply them separately with blood. At least three further passages are provided in the dilation unit disposed on the proximal side, one serves for introducing an ablation instrument, another for introducing an observation and/or rinsing unit, and a third one for introducing a drainage.

Via an inflow and outflow channel I,O, blood can be sucked off inside the working volume 5, rinsings can be conducted in the working volume 5 and observation catheters and other instruments can be introduced into the working area 5. Furthermore, the passages A1 and A2 are provided for selective introduction of ablation instruments. The surgeon is thus able to selectively ablate cardiac valve areas depending on the degree of stenosis. Thus, passage A1 serves to introduce an ablation instrument 10 in the center for aortic valve ablation in the center, whereas passage A2 permits positioning an ablation instrument near the aortic wall in order to ablate the aortic valve from the side.

The individual passages projecting through the dilation unit 2 are each equipped with a fluid-tight sluice mechanism 15, which in a simplest case is based on the elasticity of the balloon material of which the dilation unit is made. Either the elastic, inflatable material snuggles, practically following the contours, to an outer circumferential edge of the inflated dilation unit 2 and of the aortic wall, such as is the case for example in FIG. 3 with reference to the passages for the coronary catheter C, or the passages are located in the middle of the dilation unit and are completely surrounded by the dilation unit and form tube-like passages in which the channel walls snuggle to each other in a fluid-tight manner in an inflated state and are pressed apart in a fluid-tight manner when a catheter is introduced. FIG. 3 shows a passage pressed apart in a fluid tight matter for one coronary catheter C and other passages I, O, A1, A2 and shows a passage that is sealed fluid-tight without the provision of a second coronary catheter C. Thus, the sluice mechanism seals passages fluid-tight without the provision of an auxiliary catheter when the dilation unit disposed on the proximal side is in an inflated state.

Figure 5:
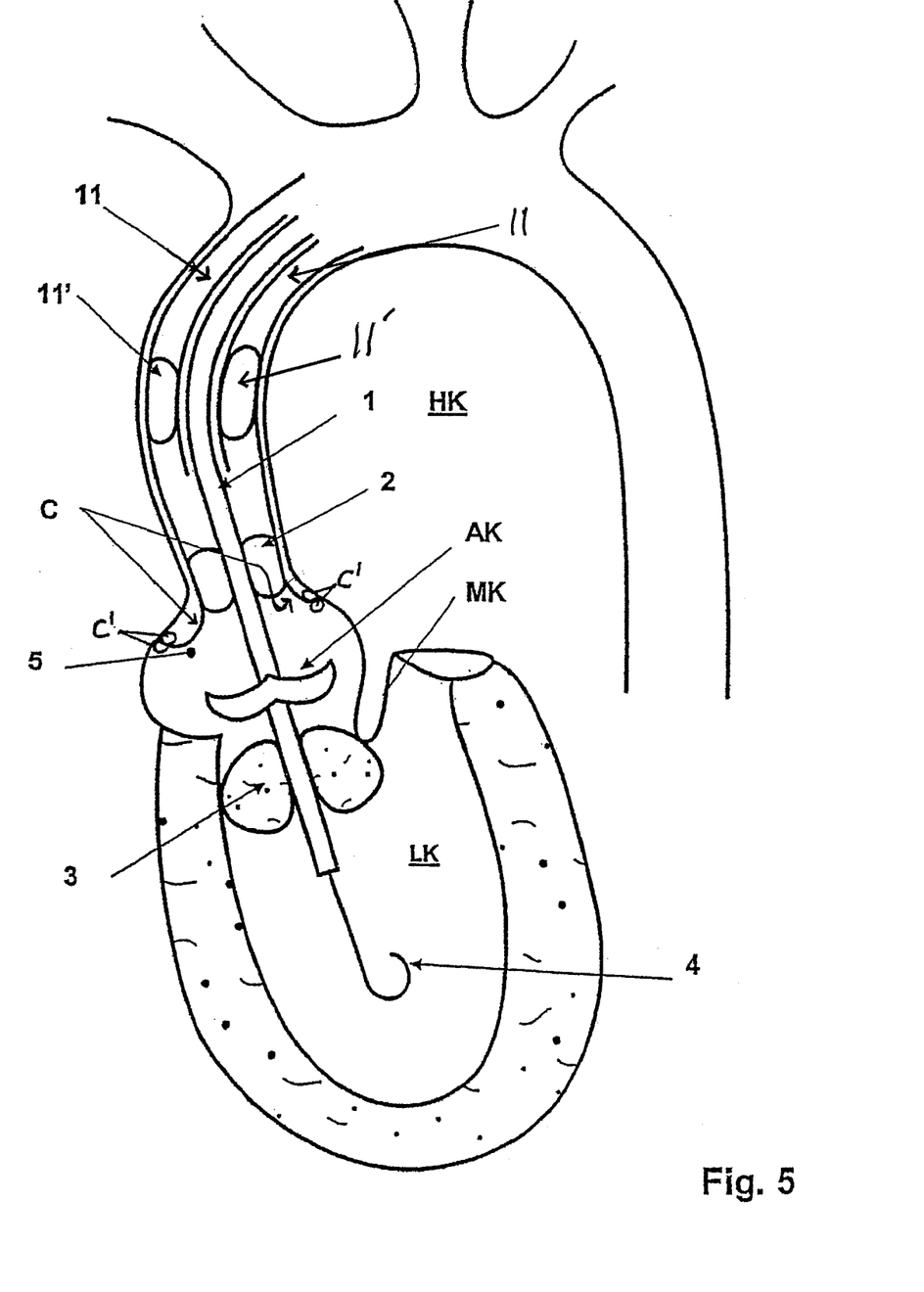

With reference to FIG. 5, in which the vessel regions involved in a cardiac valve extraction are shown very schematically, the operation steps required for conducting successful cardiac valve surgery will be described.

After corresponding positioning of a guiding catheter 4, which has been introduced from the abdominal region into the left ventricle LK of a patient, the perfusion catheter 1 designed according to the present invention is positioned at the site of the aortic valve AK in the aforedescribed manner. In the same manner, prior to inflating the dilation units 2,3 of the perfusion catheter 1, two coronary perfusion catheters C are connected to the left coronary artery, respectively the right coronary artery, to supply the coronaries with blood. In the following, then dilation units 2,3 are inflated and corresponding auxiliary catheters are introduced into the working volume 5 bordered by the two dilation units 2,3. The working volume 5 bordered by the two dilation units 2,3 is pumped empty of blood with the aid of a suction catheter so that the surgeon can ablate the stenosed cardiac valve under viewing conditions using suited ablation instruments. The ablated cardiac valve fragments are conveyed extracorporeally via a suited rinsing line projecting through the dilation unit 2 in such a manner that any risk of embolism can be completely ruled out.

After corresponding total or partial extraction of the cardiac valve, an externally controllable sluice element 11 is introduced into the ascending aorta for interim maintenance of the cardiac valve function. The sluice element 11 is provided with a dilation element 11' which can be triggered with the aid of an EKG device. Following deflation of the dilation units 2,3 of the perfusion catheter 1, the perfusion catheter 1 is removed extracoporeally, with the sluice element 11 remaining inside the ascending aorta and taking over at least temporarily cardiac valve function until a cardiac valve prosthesis is implanted at the site of the natural cardiac valve.

Figure 6:
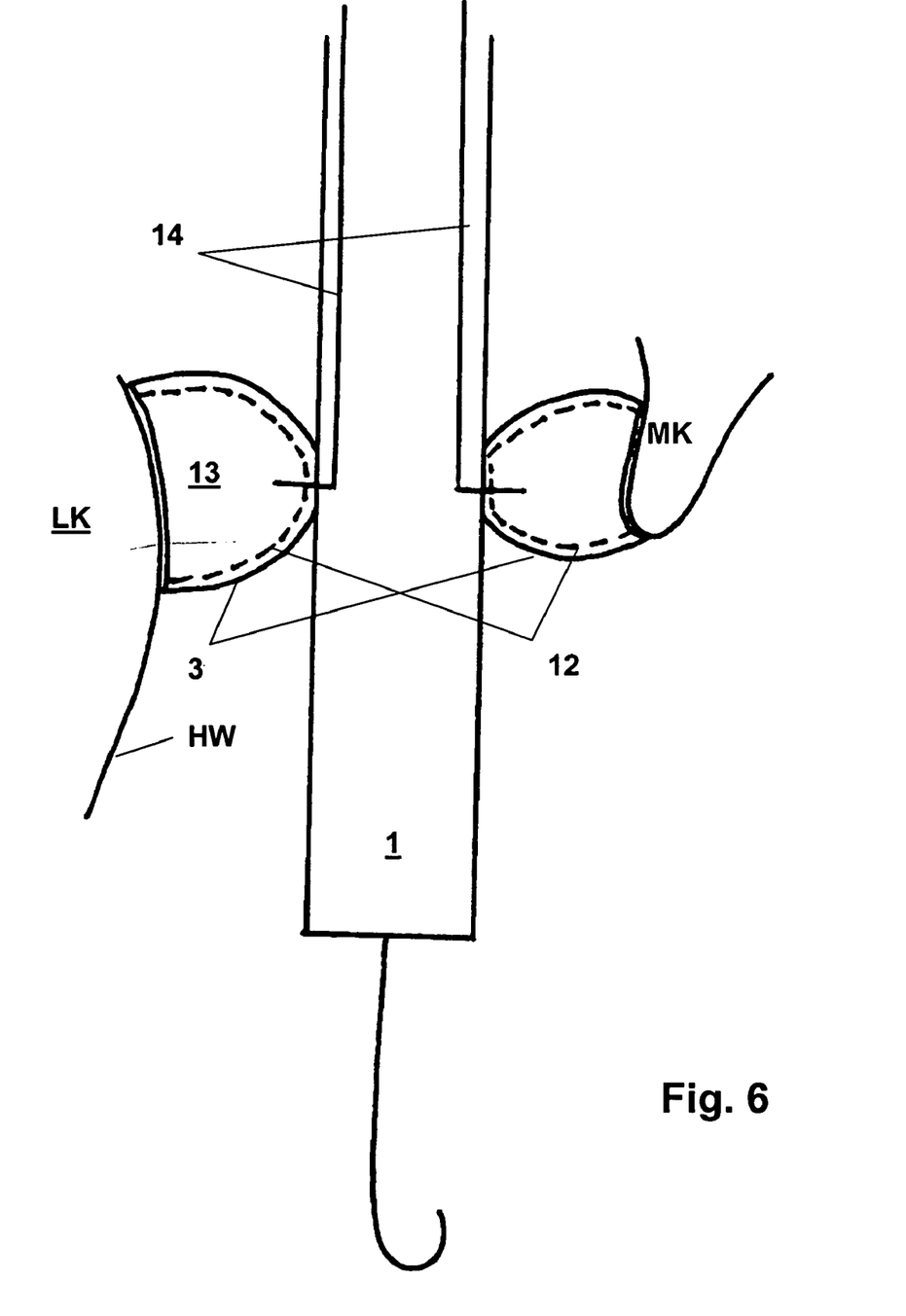

FIG. 6 shows an alternative preferred embodiment of a dilation unit designed as a balloon element 2,3 with reference to the preceding figures. The aim is in particular to produce in the region of the entrance to the left ventricle LK, a fluid-tight occlusion between the ventricle wall on the one hand and the region of the mitral valve to the balloon element 3 on the other hand (see FIG. 5), for instance in particular the mitral valve region that comes into contact with the balloon element 3 could yield, thereby rendering the desired occlusion unsatisfactory. Particularly in this case, a solution is a dilation unit designed as a suction element as shown in FIG. 6.

FIG. 6 shows the distal region of the perfusion catheter 1 projecting into the left ventricle LK. The dilation unit 3 is designed as a ring-shaped suction element, with a bell-shaped cross section, enclosing the perfusion catheter 1. The suction element comprises a double-walled tube structure made of an elastic material. The tube volume 12 of the wall-structure is inflatable. Furthermore, connected to the half-open bell-interior 13 is a suction line 14 which provides the bell interior 13 with vacuum enabling the elastic tube structure to snuggle closely to the counter wall. In the case shown in FIG. 6, the suction element is able to enter close contact, on the one hand, with the inner ventricle wall HW, and, on the other hand, with regions of the mitral valve MK. There is no displacement as in the case of the balloon element.

In detail the method for cardiac valve replacement occurs by means of the following steps:
  introduction of a coronary artery perfusion catheter into the right and the left coronary artery respectively and inflation of a cuff provided at each of the coronary artery perfusion catheters, with blood flow being ensured through the respective coronary artery perfusion catheter into the coronary arteries,
  intravascular introduction of a perfusion catheter provided near its distal end with two dilation units at a distance from each other in the longitudinal direction of the catheter,
  positioning of the perfusion catheter inside the aorta in such a manner that the aortic valve is surrounded on both sides inside the aorta by the dilation units,
  inflating the two dilation units in such a manner that the dilation units lie close to the aortic wall in a fluid-tight manner,
  emptying the blood volume enclosed by the two dilation units to create a working volume by means of introducing at least one auxiliary catheter projecting through a dilation unit disposed on the proximal side, and
  severing the aortic valve inside the working volume by means of introducing at least one cutting instrument projecting through a dilation unit disposed on the proximal side.

Preferably severing of the aortic valve occurs under optical observation by means of an optic catheter whose distal end projects into the working volume. This distinguishes the method, i.e. from all other hitherto known methods as it obviates using any visualization technology that additionally burden the patient, for example radioscopy, for controlled monitoring of the minimally invasive operation.

LIST OF REFERENCE NUMBERS 1 perfusion catheter
2,3 dilation units
4 guiding catheter
5 working volume, working region
6 blood suction opening
7 blood outlet opening
8 working channel
9 opening of the working channel
10 ablation instrument
11 sluice element
11' dilation element
12 tube volume
13 bell interior
14 suction line
A ascending aorta
AK aortic valve
$A_1, A_2, I, O$ passages
C perfusion catheter
C' cuff
D distal side
LK left ventricle
LVOT left ventricular outflow tract
P proximal side
R ring-shaped sluice, ring seal
T separation line
MK mitral valve
HK ventricle
HW ventricle wall

What is claimed is:

1. A device for minimally invasive, intravascular aortic valve extraction inside the aorta comprising:
  a perfusion catheter having at least one perfusion channel designed as a hollow channel; and
  at least two dilation units disposed at a distance from each other at the distal catheter region in the longitudinal extension of said catheter, both said dilation units being projected through by said perfusion catheter and forming, in an inflated state, an at least practically fluid-tight occlusion with the aortic wall,
  wherein at least a dilation unit disposed on the proximal side comprises an elastic, inflatable material and is provided with at least one passage outside of said perfusion catheter,
  wherein said at least one passage projects through said dilation unit disposed on the proximal side and is completely surrounded by said dilation unit disposed on the proximal side and through which at least one auxiliary catheter can be introduced for aortic valve ablation in a fluid-tight manner, and
  wherein the elastic, inflatable material of the dilation unit disposed on the proximal side seals said at least one passage fluid-tight without the provision of an auxiliary catheter when the dilation unit disposed on the proximal side is in an inflated state.

2. The device according to claim 1, wherein said at least two dilation units are balloon elements which are inflatable with a medium and are disposed at a distance of at least 1 cm from each other in the longitudinal extension of said perfusion catheter.

3. The device according to claim 1, further comprising at least one passage provided at the circumferential edge of said dilation unit disposed on the proximal side, and
  wherein, when said dilation unit is in an inflated state, part of said at least one passage is bound sickle-like by said circumferential edge of said dilation unit and a remaining part of the at least one passage is bound by said aortic wall.

4. The device according to claim 1, wherein said at least one passage is disposed in a rotatable manner about the perfusion catheter with the aid of a rotatable ring seal.

5. The device according to claim 1, wherein at least said dilation unit disposed on the proximal side is disposed in a rotary moveable manner about said perfusion catheter.

6. The device according to claim 1, wherein inside said at least one perfusion channel of said perfusion catheter a pump device is provided and
wherein on the proximal side to said dilation unit disposed on the distal side an opening is provided through which a blood flow enters said perfusion catheter and exits said perfusion catheter on the proximal side at an opening.

7. The device according to claim 1,
wherein said dilation unit disposed on the proximal side is provided with two passages for fluid-tight introduction of a coronary perfusion catheter provided at a circumferential edge, each coronary perfusion catheter provided at a distal end with a dilatable cuff,
wherein at least three further passages are provided in said dilation unit disposed on the proximal side, of said three further passages one serves for introducing an ablation instrument, another for introducing an observation and/or rinsing unit, and a third one for introducing a drainage,
wherein said at least three further passages project through said dilation unit disposed on the proximal side and are completely surrounded by said dilation unit disposed on the proximal side.

8. The device according to claim 1, wherein said perfusion catheter is provided with a working channel having an outlet opening in the region between the two dilation units through which at least one auxiliary catheter can be introduced for aortic valve ablation.

9. The device according to claim 1, wherein said at least one passage forms a tube whose channel walls snuggle to each other in a fluid-tight manner in an inflated state and are pressed apart in a fluid-tight manner when an auxiliary catheter is introduced.

10. The device according to claim 1, wherein said dilation units are connected each to a supply line through which a medium is introduced for inflating.

11. The device according to claim 1, wherein said dilation units are designed as suction elements which can be inflated with a medium and which have a bell-shaped cross section into whose half-open bell interior a suction line runs.

12. The device according to claim 11, wherein said suction elements comprise a double-walled tube structure made of an elastic material and encloses an inflatable volume.

13. A device according to claim 1, further comprising at least three passages in said dilation unit disposed on the proximal side, wherein said at least three passages project through said dilation unit disposed on the proximal side and are completely surrounded by said dilation unit disposed on the proximal side.

14. A device for aortic valve extraction, comprising:
a device according to claim 13;
an ablation instrument in a passage projecting through said dilation unit disposed on the proximal side and completely surrounded by said dilation unit disposed on the proximal side;
an optical observation catheter in a passage projecting through said dilation unit disposed on the proximal side and completely surrounded by said dilation unit disposed on the proximal side;
a suction line in a passage projecting through said dilation unit disposed on the proximal side and completely surrounded by said dilation unit disposed on the proximal side; and
a rinsing line in a passage projecting through said dilation unit disposed on the proximal side and completely surrounded by said dilation unit disposed on the proximal side.

15. A device for aortic valve extraction, comprising:
a device according to claim 1; and
an ablation instrument in said at least one passage.

16. A method for minimal-invasive, intravascular aortic valve extraction inside the human aorta comprising:
introducing a coronary artery perfusion catheter having a perfusion channel into the right coronary artery and another perfusion catheter into the left coronary artery and inflating a cuff provided at each coronary artery perfusion catheter respectively, with a blood flow being ensured through said coronary artery perfusion catheters into the coronary arteries,
intravascular introducing a perfusion catheter which is provided near its distal end with two dilation units disposed at a distance from each other,
positioning said perfusion catheter inside the aorta in such a manner that the aortic valve is surrounded on both sides inside the aorta by said dilation units,
inflating both of said dilation units in such a manner that said dilation units lie close to the aortic wall in a fluid-tight manner,
emptying the blood volume inside said two dilation units by introducing at least one auxiliary catheter outside of the perfusion catheter and projecting through said dilation unit disposed on the proximal side to create a working volume, and
severing the aortic valve inside said working volume by introducing at least one cutting instrument projecting through said dilation unit disposed on the proximal side,
wherein the dilation unit disposed on the proximal side is provided with at least one passage outside of said perfusion catheter,
wherein said at least one passage projects through said dilation unit disposed on the proximal side and is completely surrounded by said dilation unit disposed on the proximal side and through which the at least one cutting instrument is introduced in a fluid-tight manner,
wherein an elastic, inflatable material of the dilation unit disposed on the proximal side seals said at least one passage fluid-tight without the provision of the at least one cutting instrument when the dilation unit disposed on the proximal side is in an inflated state.

17. A method according to claim 16, wherein said severing of the aortic valve is conducted under optical observation by an optic catheter whose distal end projects into said working volume.

* * * * *